United States Patent
Borrero et al.

(10) Patent No.: US 6,230,345 B1
(45) Date of Patent: May 15, 2001

(54) MOVEABLE PEDICURE TABLE FOR COMBINATION WITH RECLINING FACIAL BED

(76) Inventors: Maria Alba Borrero, 11322-B Westheimer, Houston, TX (US) 77077; Ilba Moreno, 9139 Western Dr., Houston, TX (US) 77080

( * ) Notice: Subject to any disclaimer, the term of this patent is extended or adjusted under 35 U.S.C. 154(b) by 0 days.

(21) Appl. No.: 09/061,735

(22) Filed: Apr. 18, 1998

(51) Int. Cl.⁷ .............................. A47B 7/00; A47K 3/022
(52) U.S. Cl. .................. 5/613; 5/658; 5/503.1; 5/606; 5/928; 4/621; 4/645
(58) Field of Search .................. 5/613, 620, 624, 5/658, 503.1, 928, 606; 4/621, 622, 574.1, 573.1, 547, 630, 631, 645; 297/170, 174, 182, 423.4, 423.19; 108/149; 312/196; 280/188, 189

(56) References Cited

U.S. PATENT DOCUMENTS

| | | |
|---|---|---|
| 304,876 | 9/1884 | Wallace et al. |
| D. 346,043 | 4/1994 | Galati, Jr. et al. .............. D28/61 |
| 1,039,708 * | 10/1912 | Denquer ....................... 5/613 X |
| 1,879,673 | 9/1932 | Fischer . |
| 2,177,174 | 10/1939 | Eccles ......................... 155/172 |
| 2,519,771 | 8/1950 | Lacore ......................... 155/165 |
| 2,603,814 | 7/1952 | Weber ........................... 15/265 |
| 2,781,827 | 2/1957 | Bell ............................. 155/165 |
| 2,872,259 * | 2/1959 | Thorpe .......................... 5/613 |
| 3,606,458 | 9/1971 | Attinger ....................... 297/439 |
| 4,240,662 * | 12/1980 | Anderson ...................... 297/182 |
| 4,385,414 * | 5/1983 | Damico ......................... 16/35 R |
| 4,405,142 | 9/1983 | Whetstine ...................... 280/242 |
| 4,878,709 * | 11/1989 | Okamoto ...................... 297/423.19 |
| 5,378,041 | 1/1995 | Lee ............................ 297/391 |
| 5,489,140 | 2/1996 | Van Horn-Plato ............... 297/310 |
| 5,662,396 * | 9/1997 | Reeder et al. .................. 312/209 |
| 5,680,661 * | 10/1997 | Foster et al. ................... 5/613 X |
| 5,729,849 * | 3/1998 | Garakami ...................... 5/613 X |
| 5,926,866 * | 7/1999 | Chao .......................... 4/573.1 X |

FOREIGN PATENT DOCUMENTS

| | | |
|---|---|---|
| 528171 | 6/1931 | (DE) . |
| 1 088 186 | 6/1959 | (DE) . |
| 1 213 251 | 4/1969 | (GB) . |

* cited by examiner

Primary Examiner—Terry Lee Melius
Assistant Examiner—James M Hewitt
(74) Attorney, Agent, or Firm—Haynes and Boone, L.L.P.; John W. Montgomery

(57) ABSTRACT

A moveable pedicure table for combination with a reclining facial bed as provided having a table frame with side portions and a central open portion. Legs extend downward from the frame and rollers are attached to the legs for movement along a horizontal ground or floor surface. Projections extend inward into the central open area from the sides of the table frame. The projections are constructed for supporting a pedicure basin at a predetermined height. A connector mechanism is attached to the table frame for detachable engagement with a facial bed.

13 Claims, 2 Drawing Sheets

MOVEABLE PEDICURE TABLE FOR COMBINATION WITH RECLINING FACIAL BED

TECHNICAL FIELD OF THE INVENTION

The present invention relates to a beauty salon apparatus and particularly to a moveable and adjustable height pedicure table and more particularly to a moveable pedicure table that is specially constructed for detachably attachable use in combination with a reclining facial bed, and to the combination of a facial bed and pedicure table and the method of using the same.

BACKGROUND OF THE INVENTION

In the past, salon pedicures have been provided to customers while seated in a pedicure chair having a basin or pedicure bowl positioned at the foot of the chair or on a footrest for the chair.

In beauty salons in the past, facials have been provided to customers while reclining on a facial bed or a facial chair having a reclinable backrest. The time required to adequately provide a customer with a modern-day total facial treatment is often as long as one and one-half hours. The time typically required for providing a pedicure is typically about one hour or less. Typically, because of special training required for providing facials and also separately special training required for providing pedicures, one salon specialist will often provide the pedicure treatment and another specialist will provide the facial treatment. In order for a customer of the salon to receive both the facial and the pedicure treatment, the combined time of as much as three hours or more may be required.

In some salons manicures can be provided either while a customer is receiving a facial or while the customer is also receiving a pedicure. Typically however, because of the similarity between a pedicure and manicures, the operator or salon specialist providing the pedicure will, in many instances, also be the operator providing the manicure. In those situations, a manicure can be provided while the customer is receiving a facial. If the three procedures are received separately, the time spent by the customer is again increased. In the event that the manicure can be provided simultaneously with the pedicure or simultaneously with the facial, the time required for all three operations is still the time required for a facial plus the time required for a pedicure.

The construction of facial beds in the past have commonly included a cushioned seat portion, a back portion and a leg support portion. The leg support portion often folded downward to allow the customer to sit on the seat portion and upon reclining against the back portion, the foot portion could be raised to provide a horizontal footrest and position the customer on a substantially horizontal bed.

SUMMARY OF THE INVENTION

The present invention overcomes many of the drawbacks and disadvantages of the prior art by providing a combination pedicure table and facial bed by which a pedicure and a facial may be provided simultaneously and comfortably; saving time and increasing the benefit both to beauticians and to customers.

According to another aspect of the invention, the pedicure table is moveably detachable so that the same pedicurist may move the pedicure table from one facial bed, prepare the pedicure table for another customer, and move the pedicure table to another facial bed and give another pedicure. With two facial beds, one pedicurist can move from one facial client to the next with only one pedicure table to maximize the use of time.

According to another aspect of the invention, the easily moveable and detachably attachable pedicure table is constructed for providing an adjustable height pedicure basin. This conveniently permits the same pedicure table to be useful for customers having different stature or different lengths of legs.

According to another aspect of the present invention, the pedicure table is provided with casters or rollers by which it may be conveniently moved from one facial bed to another facial bed. The moveable pedicure table is further provided with detachable engagement mechanisms by which the pedicure table, once moved into position at the foot of a facial bed, can be securely held in proper position relative to the facial bed.

This way a customer can have a facial, manicure and pedicure during an appointment of only one and one-half hours duration in one room saving time and saving space. The beauty salons will be able to book more appointments during the same time with the same space and increase their business and profitability.

BRIEF DESCRIPTION OF THE DRAWINGS

These and other objects and advantages of the present invention may be more fully understood with reference to the following detailed description, claims and drawings in which like numerals represent like elements and in which:

DETAILED DESCRIPTION OF THE PREFERRED EMBODIMENTS

Figure 1:
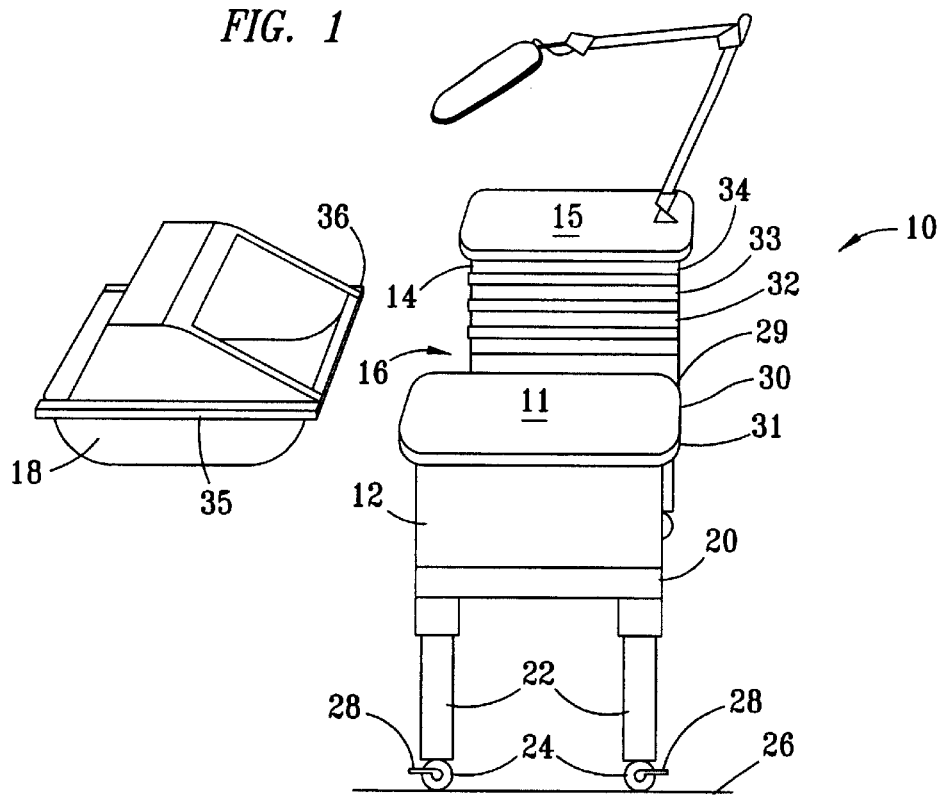
FIG. 1 is a perspective view of a moveable pedicure table according to the present invention.

FIG. 1 is a schematic perspective view of a moveable pedicure table 10 according to the present invention, having a first side portion 12 and a second side portion 14. The side portions 12 and 14 define a central opening 16 into which a pedicure bowl or basin 18 is removably held. The side portions 12 and 14 are rigidly attached to frame 20 two horizontal table portions 11 and 15, respectively. Frame 20 is moveably supported from the floor on a plurality of legs 22 with rollers or casters 24 for movement along a floor or ground surface 26. Each caster 24 is provided with a locking mechanism 28 by which the position of the moveable pedicure table 10 can be maintained at a fixed position immediately adjacent to the front of a facial bed 50 (shown in FIG. 2).

Figure 2:
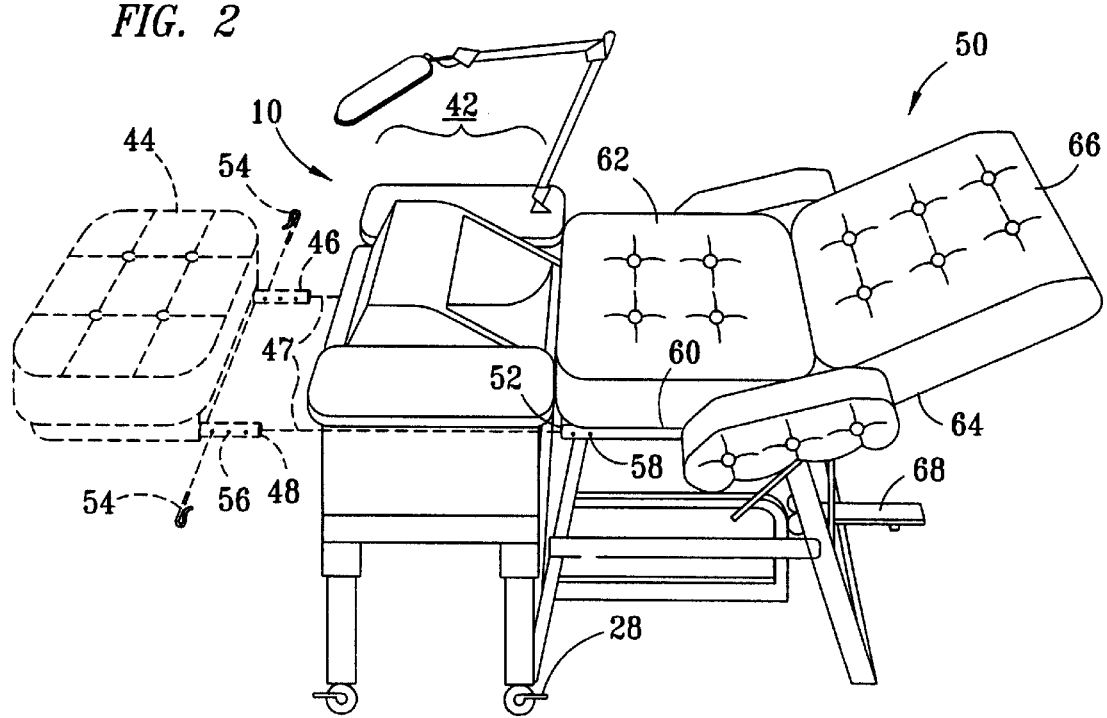
FIG. 2 is a perspective view of a detachably attachable pedicure table shown properly positioned and secured in combination with a facial table according to one embodiment of the present invention.

Pedicure basin 18 is held in position within opening 16 at a height comfortable for use in combination with a facial bed 50 (shown in FIG. 2). In the embodiment depicted a channel 30 is formed and projects inwardly from sides 12 and a parallel channel 33 projects inwardly from side 14 by which edge 35 and edge 36 projecting outwardly from basin 18 may be slidably engaged into channels 30 and 33, respectively. In the preferred embodiment a first plurality of horizontal channels 29, 30 and 31 projecting inward from side 12 and a second plurality of horizontal channels 32, 33 and 34 projecting inwardly into opening 16 from side 14. With opposing pairs of these channels (29 and 34), (30 and 33), and (31 and 32) at different heights, the basin 18 can be selectably positioned at different heights by sliding basin edges 35 and 36 into pairs of horizontal channels 29 and 32, or horizontal channels 30 and 33, or horizontal channels 31 and 34.

The pedicure table 10 and reclining facial bed 50 are depicted in combination in FIG. 2, which is a perspective view of the combination according to one embodiment of the invention. The pedicure table 10 may be rolled from one facial bed to another on casters 24. Locking wheel mechanisms 28 are preferably cam lock type lever operated mechanisms, raised (as in FIG. 1) to allow free rolling and pushed down (as in FIGS. 2 and 4) to hold the moveable pedicure table 10 in proper position in area 42 in front of the facial bed 50 while a pedicure is given. The facial bed 50 includes a horizontal seat support 60 for supporting a seat cushion 62. There is a rear back supporting portion 64 which holds a back cushion 66. Many available facial beds have seat supports 60 that are formed with tubular members on either side along the bottom of the seat cushion. Back support 64 is adjustably positionable with adjustment mechanism 68 to allow the back cushion to be positioned for a sitting position at an angle only partially reclined from vertical, or to be positioned for lying down at an angle more fully reclined, as depicted. The moveable pedicure table 10 is positioned in a front area 42 of facial bed 50 from which any foot support 44, as might be present on a typical facial bed has been removed (shown schematically with dashed lines 47, with the footrest 44 in "mid air," without visible support from the operator as would be the normal usage situation). When the pedicure table is moved to another facial bed, the footrest 44 can be conveniently replaced using bayonet connectors 46 and 48 inserted into openings 52 formed in the support frame 60 of the facial bed 50. Existing facial beds with tubular support frame members can be adapted for this advantageous feature by removing existing foot rest,(these are often hinged to support frame 60) leaving exposed or otherwise forming open ends 52 in frame members and attaching smaller diameter bayonet tubes 46 and 48 to the footrest 44 for holding the foot cushion level with the seat cushion of the facial bed. Pin clips 54 inserted through alignable holes 56 and 58 removably hold bayonet connectors 46 and 48 inside openings 52.

Figure 3:
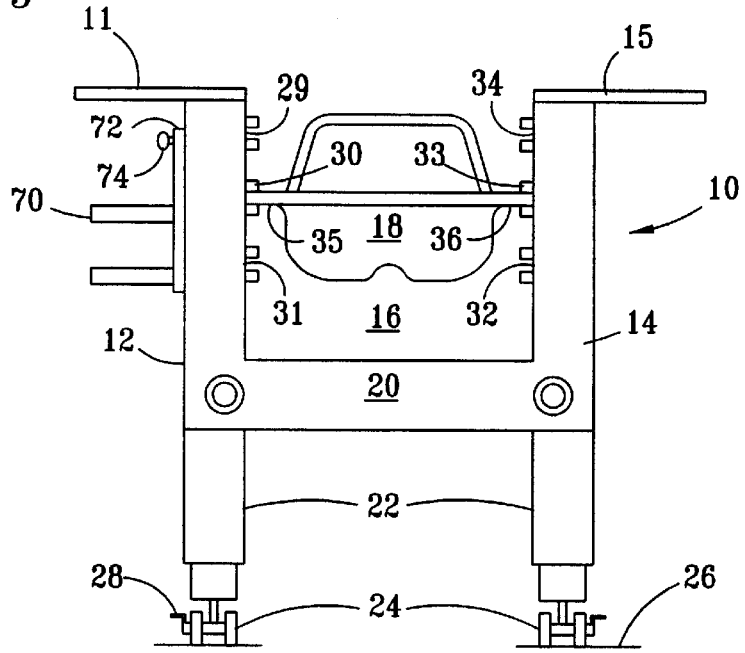
FIG. 3 is a front-end view of the pedicure table according to the present invention depicting structure for holding a pedicure basin at adjustably selectable heights and a supply holder attached to the pedicure table.

With reference to FIG. 3, which is a perspective view of an alternative embodiment of the pedicure table of FIG. 1, side portion 12 is provided with a horizontal table portion 11 and a supply rack 70 which is attached to side 12 using an attachment mechanism such as hooks to provide removability or screws to permanently affix the supply rack 70 to side 12. Also depicted schematically is the operator's moveable seat 76. The operator may release the lock mechanisms 28 to move pedicure table 10 away from facial bed 50 and roll the pedicure table to another bed to provide a pedicure to another customer. The moveable seat 76 can also be moved to the next facial bed.

Figure 4:
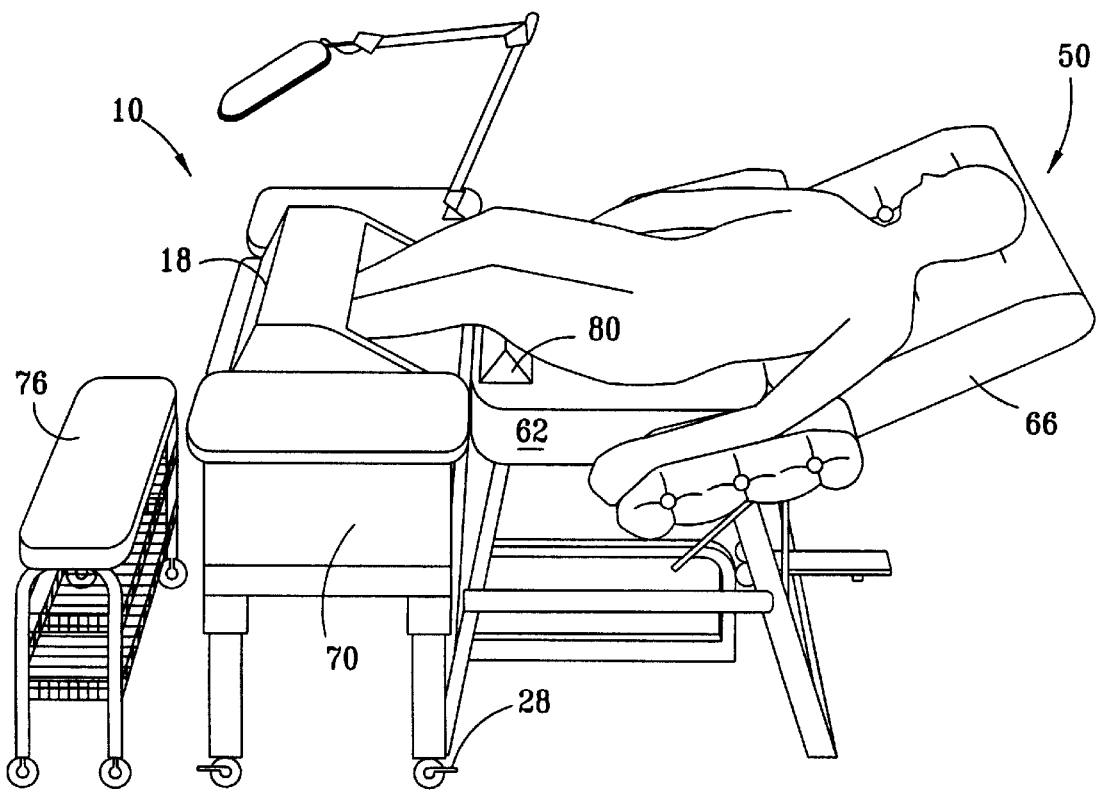
FIG. 4 is a schematic side view depicting a combination pedicure table and a facial bed in use by a person (shown in phantom lines) according to the present invention.

FIG. 4 is a schematic depiction of a pedicure table and facial bed combination in use by a person receiving a facial and simultaneously receiving a pedicure. A cushion 80 is placed under the person's knees to facilitate comfortable positioning of the person's feet for soaking and for other pedicure procedures. During only a part of the time that it takes to provide a facial, a pedicure, is completed. A manicure (not shown) can also be provided at the same time or after the pedicure is completed. If another facial bed is used, the same pedicurist can complete one pedicure using the inventive movable pedicure table 10, remove the pedicure table 10, replace foot cushion 44 using bayonet connectors 46 and 48, and move the pedicure table to another facial bed and customer.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A movable pedicure table assembly for use with a reclining facial bed for providing a person reclined on the facial bed with a pedicure, said pedicure table assembly comprising:
   a. an elevated pedicure basin specially adapted for use with the reclining facial bed, said basin being constructed and positioned at a predetermined one of a plurality of heights for comfortably receiving the reclined person's feet;
   b. a pedicure table comprising a table frame having opposed side portions, said side portions extending upward from said table frame to define a central open portion therebetween, a support structure extending downward from said table frame, and rollers attached to said support structure to permit movement of said table along a horizontal ground or floor surface;
   c. a plurality of projections extending inward into said central open portion from said side portions of said table frame, said projections being constructed for supporting said pedicure basin at one of said plurality of heights; and
   d. a locking mechanism attached to said rollers for holding said table frame adjacent to said reclining facial bed.

2. The movable pedicure table assembly as in claim 1 wherein said plurality of projections comprise at least two pairs of opposed projections, the pairs of opposed projections being vertically spaced and defining said plurality of heights.

3. The movable pedicure table assembly as in claim 2 further comprising:
   a. a horizontal table portion supported from at least one of said side portions; and
   b. a pedicure supply shelf supported by at least one of said side portions.

4. The movable pedicure table assembly as in claim 1 further comprising:
   a. a pedicure basin having first and second opposed edges and first and second parallel edge rails transverse to said opposed edges of said pedicure basin; and
   b. wherein slots are formed between said plurality of projections for engaging said opposed edges of said pedicure basin.

5. A kit comprising:
   a. a facial bed having a frame, a middle portion of said frame supporting a substantially horizontal seat cushion, and a back portion supporting a back cushion and having both a partially reclined back supported position and a substantially horizontal, fully reclined position;

b. a pedicure basin; and c. a movable pedicure table housing said pedicure basin, the table being located adjacent said middle portion of said facial bed and constructed so as to elevate said pedicure basin so that a recipient of a facial may at the same time be conveniently and comfortably provided with a pedicure using said movable pedicure table.

6. The kit of claim 5 wherein said movable pedicure table further comprises:

a. a table frame having opposed side portions which extend upward from said table frame to define a central open portion therebetween, a support structure extending downward therefrom, and rollers attached to said support structure to permit movement of said table along a horizontal ground or floor surface;

b. projections extending inward into said central open portion from said side portions of said table frame, said projections being constructed for supporting said pedicure basin at a predetermined height; and c. a locking mechanism attached to said rollers for holding said table frame adjacent said facial bed.

7. The kit of claim 6 wherein said projections comprise at least two pairs of opposed projections, the pairs of opposed projections being vertically spaced for supporting said pedicure basin at at least two different heights.

8. The kit of claim 7 further comprising:

a. a horizontal table portion supported from at least one of said side portions; and b. a pedicure supply shelf supported by at least one of said side portions of said table frame.

9. The kit of claim 6 further comprising:

a. said pedicure basin having first and second opposed edges and first and second parallel edge rails transverse to said opposed edges of said pedicure basin; and b. wherein slots are formed between said projections for engaging said opposed edges of said pedicure basin.

10. The kit of claim 5 further comprising:

a. a footrest having bayonet connectors projecting therefrom; and b. said facial bed having a front portion with openings for detachably receiving said bayonet connectors to hold said footrest adjacent said horizontal seat cushion when said pedicure table is not adjacent said facial bed.

11. The kit of claim 5 wherein said movable pedicure table further comprises a means for locking said pedicure table adjacent said facial bed.

12. In a kit for providing pedicures to a recipient using a pedicure basin, the kit comprising:

a. a reclining facial bed having a frame, a middle portion of said frame supporting a substantially horizontal seat cushion, and a back portion supporting a back cushion in either a partially reclined or substantially horizontal position; and b. a pedicure table supporting an elevated pedicure basin that is vertically adjustable for purposes of comfortably placing the reclining pedicure recipient's feet in said pedicure basin such that the recipient may receive both a facial and a pedicure simultaneously.

13. A method of providing a combined facial and pedicure to a recipient comprising:

a. locating the recipient on a reclining facial bed normally used in the beauty salon industry but modified so as to be compatible with a pedicure table housing an elevated and vertically adjustable pedicure basin, said pedicure table being adjacent said facial bed;

b. selectively adjusting the vertical position of said pedicure basin within said pedicure table such that a pedicure recipient's feet fit comfortably within said pedicure basin while said recipient reclines on said facial bed; and c. providing a pedicure in conjunction with another beauty salon service.

\* \* \* \* \*

UNITED STATES PATENT AND TRADEMARK OFFICE
CERTIFICATE OF CORRECTION

PATENT NO. : 6,230,345 B1  
DATED : May 15, 2001  
INVENTOR(S) : Maria Alba Borrero Iiba Moreno Page 1 of 1

It is certified that error appears in the above-identified patent and that said Letters Patent is hereby corrected as shown below:

Column 2,  
Line 54, "rigidly attached to frame 20" should be -- rigidly attached projecting upwardly from frame 20 --.

Signed and Sealed this

Eighth Day of January, 2002

*Attest:*

*Attesting Officer*

JAMES E. ROGAN  
*Director of the United States Patent and Trademark Office*